(12) United States Patent  
Cole

(10) Patent No.: US 9,895,267 B2
(45) Date of Patent: *Feb. 20, 2018

(54) WELDING HELMET WITH INTEGRAL USER INTERFACE

(71) Applicant: LINCOLN GLOBAL, INC., City of Industry, CA (US)

(72) Inventor: Stephen R. Cole, University Heights, OH (US)

(73) Assignee: Lincoln Global, Inc., City of Industry, CA (US)

( * ) Notice: Subject to any disclaimer, the term of this patent is extended or adjusted under 35 U.S.C. 154(b) by 1000 days.

This patent is subject to a terminal disclaimer.

(21) Appl. No.: 14/037,699

(22) Filed: Sep. 26, 2013

(65) Prior Publication Data

US 2014/0013478 A1    Jan. 16, 2014

Related U.S. Application Data

(63) Continuation of application No. 12/577,824, filed on Oct. 13, 2009, now Pat. No. 8,569,655.

(51) Int. Cl.
*A61F 9/06* (2006.01)
*F16P 1/06* (2006.01)
*B23K 37/06* (2006.01)
*B23K 9/095* (2006.01)
*B23K 9/32* (2006.01)

(52) U.S. Cl.
CPC ............. *A61F 9/06* (2013.01); *B23K 9/0953* (2013.01); *B23K 9/322* (2013.01); *F16P 1/06* (2013.01)

(58) Field of Classification Search
CPC ......... A61F 9/06; B23K 9/0953; B23K 9/322; B23K 37/006; F16P 1/06

See application file for complete search history.

(56) References Cited

U.S. PATENT DOCUMENTS

| | | |
|---|---|---|
| 1,159,119 A | 11/1915 | Springer |
| D140,630 S | 3/1945 | Garibay |
| D142,377 S | 9/1945 | Dunn |
| D152,049 S | 12/1948 | Welch |
| 2,681,969 A | 6/1954 | Burke |
| D174,208 S | 3/1955 | Abidgaard |
| 2,728,838 A | 12/1955 | Barnes |
| D176,942 S | 2/1956 | Cross |
| 2,894,086 A | 7/1959 | Rizer |
| 3,035,155 A | 5/1962 | Hawk |
| 3,059,519 A | 10/1962 | Stanton |

(Continued)

FOREIGN PATENT DOCUMENTS

| | | |
|---|---|---|
| CA | 2698078 | 9/2011 |
| CN | 101209512 A | 7/2008 |

(Continued)

OTHER PUBLICATIONS

ViziTech USA, retrieved on Mar. 27, 2014 from http://vizitechusa.com/, 2 pages.

(Continued)

*Primary Examiner* — Geoffrey S Evans

(57) ABSTRACT

A welding helmet is capable of providing an image representative of information from an associated welding operation where the image appears in the same focal range as the welding work area.

13 Claims, 6 Drawing Sheets

(56) References Cited

U.S. PATENT DOCUMENTS

| | | |
|---|---|---|
| 3,356,823 A | 12/1967 | Waters et al. |
| 3,555,239 A | 1/1971 | Kerth |
| 3,621,177 A | 11/1971 | McPherson et al. |
| 3,654,421 A | 4/1972 | Streetman et al. |
| 3,739,140 A | 6/1973 | Rotilio |
| 3,866,011 A | 2/1975 | Cole |
| 3,867,769 A | 2/1975 | Schow et al. |
| 3,904,845 A | 9/1975 | Minkiewicz |
| 3,988,913 A | 11/1976 | Metcalfe et al. |
| D243,459 S | 2/1977 | Bliss |
| 4,024,371 A | 5/1977 | Drake |
| 4,041,615 A | 8/1977 | Whitehill |
| D247,421 S | 3/1978 | Driscoll |
| 4,124,944 A | 11/1978 | Blair |
| 4,132,014 A | 1/1979 | Schow |
| 4,237,365 A | 12/1980 | Lambros et al. |
| 4,275,266 A | 6/1981 | Lasar |
| 4,280,041 A | 7/1981 | Kiesslilng et al. |
| 4,280,137 A | 7/1981 | Ashida et al. |
| 4,314,125 A | 2/1982 | Nakamura |
| 4,359,622 A | 11/1982 | Dostoomian et al. |
| 4,375,026 A | 2/1983 | Kearney |
| 4,410,787 A | 10/1983 | Kremers et al. |
| 4,429,266 A | 1/1984 | Traadt |
| 4,452,589 A | 6/1984 | Denison |
| D275,292 S | 8/1984 | Bouman |
| D277,761 S | 2/1985 | Korovin et al. |
| 4,523,808 A | 6/1985 | Miller |
| D280,329 S | 8/1985 | Bouman |
| 4,611,111 A | 9/1986 | Baheti et al. |
| 4,616,326 A | 10/1986 | Meier et al. |
| 4,629,860 A | 12/1986 | Lindbom |
| 4,641,282 A | 2/1987 | Ounuma |
| 4,677,277 A | 6/1987 | Cook et al. |
| 4,680,014 A | 7/1987 | Paton et al. |
| 4,689,021 A | 8/1987 | Vasiliev et al. |
| 4,707,582 A | 11/1987 | Beyer |
| 4,716,273 A | 12/1987 | Paton et al. |
| D297,704 S | 9/1988 | Bulow |
| 4,867,685 A | 9/1989 | Brush et al. |
| 4,877,940 A | 10/1989 | Bangs et al. |
| 4,897,521 A | 1/1990 | Burr |
| 4,907,973 A | 3/1990 | Hon |
| 4,931,018 A | 6/1990 | Herbst |
| 4,998,050 A | 3/1991 | Nishiyama et al. |
| 5,034,593 A | 7/1991 | Rice et al. |
| 5,061,841 A | 10/1991 | Richardson |
| 5,089,914 A | 2/1992 | Prescott |
| 5,192,845 A | 3/1993 | Kirmsse et al. |
| 5,206,472 A | 4/1993 | Myking et al. |
| 5,266,930 A | 11/1993 | Ichikawa et al. |
| 5,285,916 A | 2/1994 | Ross |
| 5,305,183 A | 4/1994 | Teynor |
| 5,320,538 A | 6/1994 | Baum |
| 5,337,611 A | 8/1994 | Fleming et al. |
| 5,360,156 A | 11/1994 | Ishizaka et al. |
| 5,360,960 A | 11/1994 | Shirk |
| 5,370,071 A | 12/1994 | Ackermann |
| D359,296 S | 6/1995 | Witherspoon |
| D395,296 S | 6/1995 | Witherspoon |
| 5,424,634 A | 6/1995 | Goldfarb et al. |
| 5,436,638 A | 7/1995 | Bolas et al. |
| 5,464,957 A | 11/1995 | Kidwell et al. |
| D365,583 S | 12/1995 | Viken |
| 5,562,843 A | 10/1996 | Yasumoto |
| 5,670,071 A | 9/1997 | Ueyama et al. |
| 5,671,158 A | 9/1997 | Fournier |
| 5,676,503 A | 10/1997 | Lang |
| 5,676,867 A | 10/1997 | Allen |
| 5,708,253 A | 1/1998 | Bloch et al. |
| 5,710,405 A | 1/1998 | Solomon et al. |
| 5,719,369 A | 2/1998 | White et al. |
| D392,534 S | 3/1998 | Degen et al. |
| 5,728,991 A | 3/1998 | Takada et al. |
| 5,734,421 A | 3/1998 | Maguire, Jr. |
| 5,751,258 A | 5/1998 | Fergason et al. |
| D396,238 S | 7/1998 | Schmitt |
| 5,781,258 A | 7/1998 | Debral et al. |
| 5,823,785 A | 10/1998 | Matherne, Jr. |
| 5,835,077 A | 11/1998 | Dao et al. |
| 5,835,277 A | 11/1998 | Hegg |
| 5,845,053 A | 12/1998 | Watanabe et al. |
| 5,896,579 A | 4/1999 | Johnson |
| 5,963,891 A | 10/1999 | Walker et al. |
| 6,008,470 A | 12/1999 | Zhang et al. |
| 6,049,059 A | 4/2000 | Kim |
| 6,051,805 A | 4/2000 | Vaidya et al. |
| 6,114,645 A | 9/2000 | Burgess |
| 6,155,475 A | 12/2000 | Ekelof et al. |
| 6,155,928 A | 12/2000 | Burdick |
| 6,230,327 B1 | 5/2001 | Briand |
| 6,236,013 B1 | 5/2001 | Delzenne |
| 6,236,017 B1 | 5/2001 | Smartt et al. |
| 6,242,711 B1 | 6/2001 | Cooper |
| 6,271,500 B1 | 8/2001 | Hirayama et al. |
| 6,330,938 B1 | 12/2001 | Nerve et al. |
| 6,330,966 B1 | 12/2001 | Eissfeller |
| 6,331,848 B1 | 12/2001 | Stove et al. |
| D456,428 S | 4/2002 | Aronson et al. |
| 6,373,465 B2 | 4/2002 | Jolly et al. |
| D456,828 S | 5/2002 | Aronson et al. |
| 6,397,186 B1 | 5/2002 | Bush |
| D461,383 S | 8/2002 | Balckburn |
| 6,441,342 B1 | 8/2002 | Hsu |
| 6,445,964 B1 | 9/2002 | White et al. |
| 6,492,618 B1 | 12/2002 | Flood et al. |
| 6,506,997 B2 | 1/2003 | Matsuyama |
| 6,552,303 B1 | 4/2003 | Blankenship et al. |
| 6,560,029 B1 | 5/2003 | Dobbie et al. |
| 6,563,489 B1 | 5/2003 | Latypov et al. |
| 6,568,846 B1 | 5/2003 | Cote et al. |
| D475,726 S | 6/2003 | Suga et al. |
| 6,572,379 B1 | 6/2003 | Sears et al. |
| 6,583,386 B1 | 6/2003 | Ivkovich |
| 6,621,049 B2 | 9/2003 | Suzuki |
| 6,624,388 B1 | 9/2003 | Blankenship et al. |
| D482,171 S | 11/2003 | Vui et al. |
| 6,647,288 B2 | 11/2003 | Madill et al. |
| 6,649,858 B2 | 11/2003 | Wakeman |
| 6,655,645 B1 | 12/2003 | Lu et al. |
| 6,660,965 B2 | 12/2003 | Simpson |
| 6,697,701 B2 | 2/2004 | Hillen et al. |
| 6,697,770 B1 | 2/2004 | Nagetgaal |
| 6,703,585 B2 | 3/2004 | Suzuki |
| 6,708,385 B1 | 3/2004 | Lemelson |
| 6,710,298 B2 | 3/2004 | Eriksson |
| 6,710,299 B2 | 3/2004 | Blankenship et al. |
| 6,715,502 B1 | 4/2004 | Rome et al. |
| 6,720,878 B2 | 4/2004 | Jumpertz |
| D490,347 S | 5/2004 | Meyers |
| 6,730,875 B2 | 5/2004 | Hsu |
| 6,734,393 B1 | 5/2004 | Friedl et al. |
| 6,744,011 B1 | 6/2004 | Hu et al. |
| 6,750,428 B2 | 6/2004 | Okamoto et al. |
| 6,772,802 B2 | 8/2004 | Few |
| 6,788,442 B1 | 9/2004 | Potin et al. |
| 6,795,778 B2 | 9/2004 | Dodge et al. |
| 6,798,974 B1 | 9/2004 | Nakano et al. |
| 6,857,553 B1 | 2/2005 | Hartman et al. |
| 6,858,817 B2 | 2/2005 | Blankenship et al. |
| 6,865,926 B2 | 3/2005 | O'Brien et al. |
| 6,871,958 B2 | 3/2005 | Christensen |
| D504,449 S | 4/2005 | Butchko |
| 6,920,371 B2 | 7/2005 | Hillen et al. |
| 6,940,039 B2 | 9/2005 | Blankenship et al. |
| 7,021,937 B2 | 4/2006 | Simpson et al. |
| 7,126,078 B2 | 10/2006 | Demers et al. |
| 7,132,617 B2 | 11/2006 | Lee et al. |
| 7,170,032 B2 | 1/2007 | Flood |
| 7,194,447 B2 | 3/2007 | Harvey et al. |
| 7,247,814 B2 | 7/2007 | Ott |
| D555,446 S | 11/2007 | Picaza Ibarrondo |
| 7,315,241 B1 | 1/2008 | Daily et al. |
| D561,973 S | 2/2008 | Kinsley et al. |

(56) References Cited

U.S. PATENT DOCUMENTS

| | | |
|---|---|---|
| 7,346,972 B2 | 3/2008 | Inget |
| 7,353,715 B2 | 4/2008 | Myers |
| 7,363,137 B2 | 4/2008 | Brant et al. |
| 7,375,304 B2 | 5/2008 | Kainec et al. |
| 7,381,923 B2 | 6/2008 | Gordon et al. |
| 7,414,595 B1 | 8/2008 | Muffler |
| 7,465,230 B2 | 12/2008 | LeMay et al. |
| 7,478,108 B2 | 1/2009 | Townsend et al. |
| D587,975 S | 3/2009 | Aronson et al. |
| 7,516,022 B2 | 4/2009 | Lee et al. |
| D602,057 S | 10/2009 | Osicki |
| 7,621,171 B2 | 11/2009 | O'Brien |
| D606,102 S | 12/2009 | Bender et al. |
| 7,643,890 B1 | 1/2010 | Hillen et al. |
| 7,687,741 B2 | 3/2010 | Kainec et al. |
| D614,217 S | 4/2010 | Peters et al. |
| D615,573 S | 5/2010 | Peters et al. |
| 7,817,162 B2 | 10/2010 | Bolick et al. |
| 7,853,645 B2 | 12/2010 | Brown et al. |
| D631,074 S | 1/2011 | Peters et al. |
| 7,874,921 B2 | 1/2011 | Baszucki et al. |
| 7,926,118 B2 | 4/2011 | Becker |
| 7,970,172 B1 | 6/2011 | Hendrickson |
| 7,972,129 B2 | 7/2011 | O'Donoghue |
| 7,991,587 B2 | 8/2011 | Ihn |
| 8,069,017 B2 | 11/2011 | Hallquist |
| 8,224,881 B1 | 7/2012 | Spear et al. |
| 8,248,324 B2 | 8/2012 | Nangle |
| 8,265,886 B2 | 9/2012 | Bisiaux et al. |
| 8,274,013 B2 | 9/2012 | Wallace |
| 8,287,522 B2 | 10/2012 | Moses et al. |
| 8,316,462 B2 | 11/2012 | Becker |
| 8,363,048 B2 | 1/2013 | Gering |
| 8,365,603 B2 | 2/2013 | Lesage et al. |
| 8,512,043 B2 | 8/2013 | Choquet |
| 8,569,646 B2 | 10/2013 | Daniel et al. |
| 8,569,655 B2 * | 10/2013 | Cole ................ A61F 9/06 2/8.2 |
| 8,777,629 B2 | 7/2014 | Kreindl et al. |
| 2001/0045808 A1 | 11/2001 | Hietmann et al. |
| 2001/0052893 A1 | 12/2001 | Jolly et al. |
| 2002/0032553 A1 | 3/2002 | Simpson et al. |
| 2002/0046999 A1 | 4/2002 | Veikkolainen et al. |
| 2002/0050984 A1 | 5/2002 | Roberts |
| 2002/0085843 A1 | 7/2002 | Mann |
| 2002/0175897 A1 | 11/2002 | Pelosi |
| 2003/0000931 A1 | 1/2003 | Ueda et al. |
| 2003/0001950 A1 * | 1/2003 | Eriksson ................ A61F 9/06 348/61 |
| 2003/0011673 A1 * | 1/2003 | Eriksson ................ B23K 9/32 348/42 |
| 2003/0023592 A1 | 1/2003 | Modica et al. |
| 2003/0025884 A1 | 2/2003 | Hamana et al. |
| 2003/0106787 A1 | 6/2003 | Santilli |
| 2003/0111451 A1 | 7/2003 | Blankenship et al. |
| 2003/0172032 A1 | 9/2003 | Choquet |
| 2003/0206491 A1 | 11/2003 | Pacheco |
| 2003/0234885 A1 | 12/2003 | Pilu |
| 2004/0020907 A1 | 2/2004 | Zauner et al. |
| 2004/0035990 A1 | 2/2004 | Ackeret |
| 2004/0050824 A1 | 3/2004 | Samler |
| 2004/0140301 A1 | 7/2004 | Blankenship et al. |
| 2005/0007504 A1 | 1/2005 | Fergason |
| 2005/0017152 A1 | 1/2005 | Fergason |
| 2005/0046584 A1 | 3/2005 | Breed |
| 2005/0050168 A1 | 3/2005 | Wen et al. |
| 2005/0101767 A1 | 5/2005 | Clapham et al. |
| 2005/0103766 A1 | 5/2005 | Iizuka et al. |
| 2005/0103767 A1 | 5/2005 | Kainec et al. |
| 2005/0109735 A1 | 5/2005 | Flood |
| 2005/0128186 A1 | 6/2005 | Shahoian et al. |
| 2005/0133488 A1 | 7/2005 | Blankenship |
| 2005/0159840 A1 | 7/2005 | Lin et al. |
| 2005/0189336 A1 | 9/2005 | Ku |
| 2005/0199602 A1 | 9/2005 | Kaddani et al. |
| 2005/0230573 A1 | 10/2005 | Ligertwood |
| 2005/0252897 A1 | 11/2005 | Hsu |
| 2005/0275913 A1 | 12/2005 | Vesely et al. |
| 2005/0275914 A1 | 12/2005 | Vesely et al. |
| 2006/0014130 A1 | 1/2006 | Weinstein |
| 2006/0136183 A1 | 6/2006 | Choquet |
| 2006/0163227 A1 | 7/2006 | Hillen et al. |
| 2006/0169682 A1 | 8/2006 | Kainec et al. |
| 2006/0173619 A1 | 8/2006 | Brant et al. |
| 2006/0189260 A1 | 8/2006 | Sung |
| 2006/0207980 A1 | 9/2006 | Jacovetty et al. |
| 2006/0213892 A1 | 9/2006 | Ott |
| 2006/0214924 A1 | 9/2006 | Kawamoto et al. |
| 2006/0226137 A1 | 10/2006 | Huismann et al. |
| 2006/0252543 A1 | 11/2006 | Van Noland et al. |
| 2006/0258447 A1 | 11/2006 | Baszucki et al. |
| 2007/0034611 A1 | 2/2007 | Drius et al. |
| 2007/0038400 A1 | 2/2007 | Lee et al. |
| 2007/0045488 A1 | 3/2007 | Shin |
| 2007/0088536 A1 | 4/2007 | Ishikawa |
| 2007/0112889 A1 | 5/2007 | Cook et al. |
| 2007/0198117 A1 | 8/2007 | Wajihuddin |
| 2007/0211026 A1 | 9/2007 | Ohta |
| 2007/0221797 A1 | 9/2007 | Thompson et al. |
| 2007/0256503 A1 | 11/2007 | Wong et al. |
| 2007/0277611 A1 | 12/2007 | Portzgen et al. |
| 2007/0291035 A1 | 12/2007 | Vesely et al. |
| 2008/0031774 A1 | 2/2008 | Magnant et al. |
| 2008/0038702 A1 | 2/2008 | Choquet |
| 2008/0078811 A1 | 4/2008 | Hillen et al. |
| 2008/0078812 A1 | 4/2008 | Peters et al. |
| 2008/0117203 A1 | 5/2008 | Gering |
| 2008/0128398 A1 | 6/2008 | Schneider |
| 2008/0135533 A1 | 6/2008 | Ertmer et al. |
| 2008/0140815 A1 | 7/2008 | Brant et al. |
| 2008/0149686 A1 | 7/2008 | Daniel et al. |
| 2008/0203075 A1 | 8/2008 | Feldhausen et al. |
| 2008/0233550 A1 | 9/2008 | Solomon |
| 2008/0314887 A1 | 12/2008 | Stoger et al. |
| 2009/0015585 A1 | 1/2009 | Klusza |
| 2009/0021514 A1 | 1/2009 | Klusza |
| 2009/0045183 A1 | 2/2009 | Artelsmair et al. |
| 2009/0057286 A1 | 3/2009 | Ihara et al. |
| 2009/0152251 A1 | 6/2009 | Dantinne et al. |
| 2009/0173726 A1 | 7/2009 | Davidson et al. |
| 2009/0184098 A1 | 7/2009 | Daniel et al. |
| 2009/0200281 A1 | 8/2009 | Hampton |
| 2009/0200282 A1 | 8/2009 | Hampton |
| 2009/0231423 A1 * | 9/2009 | Becker ................ A61F 9/06 348/82 |
| 2009/0259444 A1 | 10/2009 | Dolansky et al. |
| 2009/0298024 A1 | 12/2009 | Batzler et al. |
| 2009/0325699 A1 | 12/2009 | Delgiannidis |
| 2010/0012017 A1 | 1/2010 | Miller |
| 2010/0012637 A1 | 1/2010 | Jaeger |
| 2010/0048273 A1 | 2/2010 | Wallace et al. |
| 2010/0062405 A1 | 3/2010 | Zboray et al. |
| 2010/0062406 A1 | 3/2010 | Zboray et al. |
| 2010/0096373 A1 | 4/2010 | Hillen et al. |
| 2010/0121472 A1 | 5/2010 | Babu et al. |
| 2010/0133247 A1 | 6/2010 | Mazumder et al. |
| 2010/0133250 A1 | 6/2010 | Sardy et al. |
| 2010/0176107 A1 | 7/2010 | Bong |
| 2010/0201803 A1 | 8/2010 | Melikian |
| 2010/0223706 A1 | 9/2010 | Becker |
| 2010/0224610 A1 | 9/2010 | Wallace |
| 2010/0276396 A1 | 11/2010 | Cooper et al. |
| 2010/0299101 A1 | 11/2010 | Shimada et al. |
| 2010/0307249 A1 | 12/2010 | Lesage et al. |
| 2011/0006047 A1 | 1/2011 | Penrod et al. |
| 2011/0060568 A1 | 3/2011 | Goldfine et al. |
| 2011/0091846 A1 | 4/2011 | Kreindl et al. |
| 2011/0114615 A1 | 5/2011 | Daniel et al. |
| 2011/0116076 A1 | 5/2011 | Chantry et al. |
| 2011/0117527 A1 | 5/2011 | Conrardy et al. |
| 2011/0122495 A1 | 5/2011 | Togashi |
| 2011/0183304 A1 | 7/2011 | Wallace et al. |
| 2011/0248864 A1 | 10/2011 | Becker et al. |
| 2011/0316516 A1 | 12/2011 | Schiefermuller et al. |

(56) References Cited

U.S. PATENT DOCUMENTS

| | | |
|---|---|---|
| 2012/0189993 A1 | 7/2012 | Kindig et al. |
| 2012/0291172 A1 | 11/2012 | Wills et al. |
| 2012/0298640 A1 | 11/2012 | Conrardy et al. |
| 2013/0026150 A1 | 1/2013 | Chantry et al. |
| 2013/0040270 A1 | 2/2013 | Albrecht |
| 2013/0075380 A1 | 3/2013 | Albrech et al. |
| 2013/0189657 A1 | 7/2013 | Wallace et al. |
| 2013/0189658 A1 | 7/2013 | Peters et al. |
| 2013/0230832 A1 | 9/2013 | Peters et al. |
| 2014/0038143 A1 | 2/2014 | Daniel et al. |
| 2014/0134580 A1 | 5/2014 | Becker |
| 2014/0263224 A1 | 9/2014 | Becker |
| 2014/0272836 A1 | 9/2014 | Becker |
| 2014/0272837 A1 | 9/2014 | Becker |
| 2014/0272838 A1 | 9/2014 | Becker |
| 2015/0056584 A1 | 2/2015 | Boulware et al. |
| 2015/0056585 A1 | 2/2015 | Boulware et al. |
| 2015/0056586 A1 | 2/2015 | Penrod et al. |

FOREIGN PATENT DOCUMENTS

| | | |
|---|---|---|
| CN | 101214178 A | 7/2008 |
| CN | 201083660 Y | 7/2008 |
| CN | 101419755 A1 | 4/2009 |
| CN | 201229711 Y | 4/2009 |
| CN | 101571887 A | 11/2009 |
| CN | 101587659 A | 11/2009 |
| CN | 103871279 A | 6/2014 |
| DE | 28 33 638 A1 | 2/1980 |
| DE | 30 46 634 A1 | 1/1984 |
| DE | 32 44 307 A1 | 5/1984 |
| DE | 35 22 581 A1 | 1/1987 |
| DE | 4037879 A1 | 6/1991 |
| DE | 196 15 069 A1 | 10/1997 |
| DE | 197 39 720 C1 | 10/1998 |
| DE | 19834205 A1 | 2/2000 |
| DE | 19834205 A1 * | 2/2000 |
| DE | 200 09 543 U1 | 8/2001 |
| DE | 10 2005 047 204 A1 | 4/2007 |
| DE | 10 2010 038 902 A1 | 2/2012 |
| DE | 202012013151 U1 | 2/2015 |
| EP | 0 108 599 A1 | 5/1984 |
| EP | 0 127 299 | 12/1984 |
| EP | 0 145 891 A1 | 6/1985 |
| EP | 319623 B1 | 10/1990 |
| EP | 0852986 A1 | 7/1998 |
| EP | 963744 A1 * | 12/1999 |
| EP | 1010490 A1 | 6/2000 |
| EP | 1 527 852 A1 | 5/2005 |
| EP | 1905533 A2 | 4/2008 |
| ES | 2 274 736 A1 | 5/2007 |
| ES | 2274736 A1 | 5/2007 |
| FR | 1456780 | 3/1965 |
| FR | 2 827 066 A1 | 1/2003 |
| FR | 2 926 660 A1 | 7/2009 |
| GB | 1 455 972 | 11/1976 |
| GB | 1 511 608 | 5/1978 |
| GB | 2 254 172 A | 9/1992 |
| GB | 2435838 A | 9/2007 |
| GB | 2 454 232 A | 5/2009 |
| GB | 2454232 A * | 5/2009 |
| JP | 2-224877 | 9/1990 |
| JP | 05-329645 | 12/1993 |
| JP | 07-047471 | 2/1995 |
| JP | 07-232270 | 9/1995 |
| JP | 08-505091 | 4/1996 |
| JP | 08-150476 | 6/1996 |
| JP | 08-132274 | 5/1998 |
| JP | 2000-167666 A | 6/2000 |
| JP | 2001-071140 A | 3/2001 |
| JP | 2002278670 A | 9/2002 |
| JP | 2003-200372 A | 7/2003 |
| JP | 2003-326362 A | 11/2003 |
| JP | 2006-006604 A | 1/2006 |
| JP | 2006-281270 A | 10/2006 |
| JP | 2007-290025 A1 | 11/2007 |
| JP | 2009-500178 A | 1/2009 |
| JP | 2009160636 A | 7/2009 |
| JP | 2012024867 A | 2/2012 |
| KR | 20090010693 | 1/2009 |
| RU | 2008 108 601 C1 | 11/2009 |
| SU | 1038963 A1 | 8/1983 |
| WO | 98/45078 | 10/1998 |
| WO | 0112376 A1 | 2/2001 |
| WO | 01/43910 | 6/2001 |
| WO | 0158400 A1 | 8/2001 |
| WO | 2006034571 A1 | 4/2006 |
| WO | 2009120921 | 1/2009 |
| WO | 2009060231 A1 | 5/2009 |
| WO | 2009149740 A1 | 12/2009 |
| WO | 2010000003 A2 | 1/2010 |
| WO | 2010044982 | 4/2010 |
| WO | 2010091493 A1 | 8/2010 |
| WO | 2011045654 A1 | 4/2011 |
| WO | 2011058433 | 5/2011 |
| WO | 2011058433 A1 | 5/2011 |
| WO | 2011067447 A1 | 6/2011 |
| WO | 2011097035 A2 | 8/2011 |
| WO | 2012082105 A1 | 6/2012 |
| WO | 2012143327 A1 | 10/2012 |
| WO | 2013014202 A1 | 1/2013 |
| WO | 2013114189 A1 | 8/2013 |
| WO | 2013175079 A1 | 11/2013 |
| WO | 2014007830 A1 | 1/2014 |
| WO | 2014019045 A1 | 2/2014 |
| WO | 2014020386 | 2/2014 |

OTHER PUBLICATIONS

United States Provisional Patent Application for "System for Characterizing Manual Welding Operations on Pipe and Other Curved Structures," U.S. Appl. No. 62/055,724, filed Sep. 26, 2014, 35 pages.

Wuhan Onew Technology Co Ltd, "ONEW-360 Welding Training Simulator" http://en.onewtech.com/_d276479751.htm as accessed on Jul. 10, 2015, 12 pages.

Miller Electric Mfg Co, "LiveArc: Welding Performance Management System" Owner's Manual, (Jul. 2014) 64 pages.

Miller Electric Mfg Co, "LiveArc Welding Performance Management System" Brochure, (Dec. 2014) 4 pages.

Steve Mann, Raymond Chun Bing Lo, Kalin Ovtcharov, Shixiang Gu, David Dai, Calvin Ngan, Tao Al, Realtime HDR (High Dynamic Range) Video for Eyetap Wearable Computers, FPGA-Based Seeing AIDS, and Glasseyes (Eyetaps), 2012 25th IEEE Canadian Conference on Electrical and Computer Engineering (CCECE), pp. 1-6, 6 pages, Apr. 29, 2012.

Kyt Dotson, Augmented Reality Welding Helmet Prototypes How Awsome the Technology Can Get, Sep. 26, 2012, Retrieved from the Internet: URL:http://siliconangle.com/blog/2012/09/26/augmented-reality-welding-helmet-prototypes-how-awesome-the-technology-can-get/,1 page, retrieved on Sep. 26, 2014.

Terrence O'Brien, "Google's Project Glass gets some more details",Jun. 27, 2012 (Jun. 27, 2012), Retrieved from the Internet: http://www.engadget.com/2012/06/27/googles-project-glass-gets-some-more-details/, 1 page, retrieved on Sep. 26, 2014.

M. Jonsson, L. Karlsson, and L-E Lindgren, Simulation of Tack Welding Procedures in Butt Joint Welding of Plates Welding Research Supplement, 7 pages, Oct. 1985.

Guu and Rokhlin, Technique for Simultaneous Real-Time Measurements of Weld Pool Surface Geometry and Arc Force, 10 pages, Dec. 1992.

D. Mavrikios, V. Karabatsou, D. Fragos and G. Chryssolouris, A prototype virtual reality-based demonstrator for immersive and interactive simulation of welding processes, International Journal of Computer Integrated Manufacturing, abstract, 1 page, Apr.-May 2006, 294-300, vol. 19, No. 3, http://eds.a.ebscohost.com/eds/pdfviewer/pdfviewer?vid=2&sid=ab8fe67b-1 f7.

S.B. Chen, L. Wu, Q. L. Wang and Y. C. Liu, Self-Learning Fuzzy Neural Networks and Computer Vision for Control of Pulsed GTAW, 9 pages, dated May 1997.

(56) References Cited

OTHER PUBLICATIONS

D'Huart, Deat, and Lium; Virtual Environment for Training, 6th International Conference, ITS 20002, 6 pages, Jun. 2002.
Konstantinos Nasios (Bsc), Improving Chemical Plant Safety Training Using Virtual REality, Thesis submitted to the University of Nottingham for the Degree of Doctor of Philosophy, 313 pages, Dec. 2001.
Nancy C. Porter, J. Allan Cote, Timothy D. Gifford, and Wim Lam, Virtual Reality Welder Training, 29 pages, dated Jul. 14, 2006.
International Search Report for PCT/IB2009/00605.
"Design and Implementation of a Video Sensor for Closed Loop Control of Back Bead Weld Puddle Width," Robert Schoder, Massachusetts, Institute of Technology, Dept. of Mechanical Engineering, May 27, 1983.
Hills and Steele, Jr.; "Data Parallel Algorithms", Communications of the ACM, Dec. 1986, vol. 29, No. 12, p. 1170.
ARS Electronica Linz GMBH, Fronius, 2 pages, May 18, 1997.
"Penetration in Spot GTA Welds during Centrifugation,"D.K. Aidun and S.A. Martin; Journal of Material Engineering and Performance vol. 7(5) Oct. 1998—597.
ASME Definitions, Consumables, Welding Positions, dated Mar. 19, 2001. See http://www.gowelding.com/asme4.htm.
Code Aster (Software) EDF (France), Oct. 2001.
The Lindoln Electric Company; CheckPoint Production Monitoring brochure; four (4) pages; http://www.lincolnelectric.com/assets/en_US/products/literature/s232.pdf; Publication S2.32; Issue Date Feb. 2012.
"Numerical Analysis of Metal Transfer in Gas Metal Arc Welding," G. Wang, P.G. Huang, and Y.M. Zhang. Departments of Mechanical and Electrical Engineering. University of Kentucky, Dec. 10, 2001.
Desroches, X.; Code-Aster, Note of use for aciculations of welding; Instruction manual U2.03 booklet: Thermomechincal; Document: U2.03.05; Oct. 1, 2003.
Fast, K. et al., "Virtual Training for Welding", Mixed and Augmented Reality, 2004, ISMAR 2004, Third IEEE and SM International Symposium on Arlington, VA, Nov. 2-5, 2004.
Cooperative Research Program, Virtual Reality Welder Training, Summary Report SR 0512, 4 pages, Jul. 2005.
Miller Electric MFG Co.; MIG Welding System features weld monitoring software; NewsRoom 2010 (Dialog® File 992); © 2011 Dialog. 2010; http://www.dialogweb.com/cgi/dwclient?reg=133233430487; three (3) pages; printed Mar. 8, 2012.
Numerical simulation to study the effect of tack welds and root gap on welding deformations and residual stresses of a pipe-flange joint by M. Abida and M. Siddique, Faculty of Mechanical Engineering, GIK Institute of Engineering Sciences and Technology, Topi, NWFP, Pakistan. Available on-line Aug. 25, 2005.
Abbas, M. et. al.; Code_Aster; Introduction to Code_Aster; User Manual; Booklet U1.0-: Introduction to Code_Aster; Document: U1.02.00; Version 7.4; Jul. 22, 2005.
Mavrikios D et al, A prototype virtual reality-based demonstrator for immersive and interactive simulation of welding processes, International Journal of Computer Integrated manufacturing, Taylor and Francis, Basingstoke, GB, vol. 19, No. 3, Apr. 1, 2006, pp. 294-300.
Virtual Reality Welder Trainer, Sessiion 5: Joining Technologies for Naval Applications: earliest date Jul. 14, 2006 (http://weayback.archive.org) by Nancy C. Porter, Edision Welding Institute; J. Allan Cote, General Dynamics Electric Boat; Timothy D. Gifford, VRSim, and Wim Lam, FCS Controls.
16th International Shop and Offshore Structures Congress: Aug. 20-25, 2006: Southhampton, UK, vol. 2 Specialist Committee V.3 Fabrication Technology Committee Mandate: T Borzecki, G. Bruce, Y.S. Han, M. Heinemann, A Imakita, L. Josefson, W. Nie, D. Olson, F. Roland, and Y. Takeda.
Ratnam and Khalid: "Automatic classification of weld defects using simulated data and an MLP neutral network." Insight vol. 49, No. 3; Mar. 2007.
Eric Linholm, John Nickolls, Stuart Oberman, and John Montrym, "NVIDIA Testla: A Unifired Graphics and Computing Architecture", IEEE Computer Society, 2008.

CS Wave, A Virtual learning tool for welding motion, 10 pages, Mar. 14, 2008.
The Fabricator, Virtual Welding, 4 pages, Mar. 2008.
N. A. Tech., P/NA.3 Process Modeling and Optimization, 11 pages, Jun. 4, 2008.
FH Joanneum, Fronius—virtual welding, 2 pages, May 12, 2008.
Eduwelding+, Training Activities with arc+ simulator; Weld Into the Future, Online Welding Simulator—A virtual training environment; 123arc.com; 6 pages, May 2008.
ChemWeb.com, Journal of Materials Engineering and Performance (v.7, #5), 3 pgs., printed Sep. 26, 2012.
Choquet, Claude; "ARC+: Today's Virtual Reality Solution for Welders" Internet Page, Jan. 1, 2008.
Juan Vicenete Rosell Gonzales, "RV-Sold: simulator virtual para la formacion de soldadores"; Deformacion Metalica, Es. vol. 34, No. 301 Jan. 1, 2008.
Training in a virtual environment gives welding students a leg up, retrieved on Apr. 12, 2010 from: http://www.thefabricator.com/article/arcwelding/virtually-welding.
Sim Welder, retrieved on Apr. 12, 2010 from: http://www.simwelder.com.
Production Monitoring 2 brochure, four (4) pages, The Lincoln Electric Company, May 2009.
International Search Report and Written Opinion from PCT/IB10/02913 dated Apr. 19, 2011.
Bjorn G. Agren; Sensor Integration for Robotic Arc Welding; 1995; vol. 5604C of Dissertations Abstracts International p. 1123; Dissertation Abs Online (Dialog® File 35): © 2012 ProQuest Info& Learning: http://dialogweb.com/cgi/dwclient?req=1331233317524; one (1) page; printed Mar. 8, 2012.
Heat and mass transfer in gas metal arc welding. Part 1: the arc by J. Hu and HI Tsai found in ScienceDirect, International Journal of Heat and Mass Transfer 50 (2007) 833-846 Available on Line on Oct. 24, 2006 http://www.web.mst.edu/~tsai/publications/HU-IJHMT-2007-1-60.pdf.
Texture Mapping by M. Ian Graham, Carnegie Mellon University Class 15-462 Computer Graphics, Lecture 10 dated Feb. 13, 2003.
Chuansong Wu: "Microcomputer-based welder training simulator", Computers in Industry, vol. 20, No. 3, Oct. 1992, pp. 321-325, XP000205597, Elsevier Science Publishers, Amsterdam, NL.
T. Borzecki, G. Bruce, YS. Han, et al., Specialist Committee V.3 Fabrication Technology Committee Mandate, Aug. 20-25, 2006, 49 pages, vol. 2, 16th International Ship and Offshore Structures Congress, Southampton, UK.
G. Wang, P.G. Huang, and Y.M. Zhang: "Numerical Analysis of Metal Transfer in Gas Metal Arc Welding": Departments of Mechanical Engineering; and Electrical and Computer Engineering, University of Kentucky, Lexington, KY 40506- 0108, Dec. 10, 2001, 10 pages.
123arc.com, "Eduwelding+ Weld Into the Future," Online Welding Simulator, Est. Jan. 2005, pp. 2.
ARC + Simulator; http://www.123arc.com/dn/depliant_ang.pdf; Est. Jan. 2000.
Antonelli et al, "A Semi-Automated Welding Station Exploiting Human-Robot Interaction," Advanced Manufacturing Systems and Technology, Jun. 23, 2011,pp. 249-260.
Echtler et al, "17 the Intelligent Welding Gun: Augmented Reality for Experimental Vehicle Construction," Virtual and Augmented Reality Applications in Manufacturing (Est. Jan. 2003) pp. 1-27.
Teeravarunyou et al, "Computer Based Welding Training System," International Journal of Industrial Engineering, Aug. 13, 2009, 16(2): 116-125.
American Welding Society, "Guide for Root Pass Welding of Pipe Without Backing," 3rd Edition, AWS D10.11M/D10.11:2007, 6 pages, Oct. 13, 2006.
AscienceTutor.com, "Virtual Welding Lab," 2 pages, Est. Jan. 2007.
Balijepalli, Arvind et al., "A Haptic Based Virtual Grinding Tool," 11th Symposium on Haptic Interfaces for Virtual Environment and Teleoperator Systems, 7 pages, Mar. 22-23, 2003.
Chironis, Nicholas P. et al., Abstract for "Mechanisms and Mechanical Devices Sourcebook," 2nd Edition, McGraw-Hill School Education Group, 11 pages, Jul. 28, 1996.
CS Wave, "The Virtual Welding Trainer," 6 pages, Est. Jan. 2007.

(56) References Cited

OTHER PUBLICATIONS

Edison Welding Institute, "E-Weld Predictor," 3 pages, Jun. 2008.
Garcia-Allende, P. Beatriz et al., "Defect Detection in Arc-Welding Processes by Means of the Line-To-Continuum Method and Feature Selection," Sensors, vol. 9, pp. 7753-7770, Sep. 29, 2009.
Hirche, Johannes et al., "Hardware Accelerated Per-Pixel Displacement Mapping," Proceedings of Graphics Interface, 8 pages, May 2004.
Mahrle, Achim et al., "The Influence of Fluid Flow Phenomena on the Laser Beam Welding Process," International Journal of Heat and Fluid Flow, vol. 23, pp. 288-297, Jun. 2002.
Mantinband, J. Y. (Yosh) et al., "Autostereoscopic Field-Sequential Display With Full Freedom of Movement or Let the Display Wear the Shutter Glasses!," SPIE 4660, Stereoscopic Displays and Virtual Reality Systems IX, pp. 246-253, May 23, 2002.
NSRP ASE, "Low-Cost Virtual Reality Welder Training System," 1 pages, Mar. 2008.
Porter, Nancy C. et al., "Virtual Reality Welder Training," Paper No. 2005-P19, 14 pages, Aug. 2005.
Praxair Technology Inc. "The RealWorld Trainer System: Real World Training Under Real Conditions" Brochure (Est. Jan. 2013) pp. 2.
Reeves, William T., "Particle Systems—A Technique for Modeling a Class of Fuzzy Objects," Computer Graphics, vol. 17, No. 3, pp. 359-375, Jul. 1983.
Rodjito, Patrick, Honors Theses for "Position Tracking and Motion Prediction Using Fuzzy Logic," Department of Computer Science, Colby College, 81 pages, Est. Jan. 2006.
Russell, Stuart J. et al., "Artificial Intelligence—A Modern Approach," Prentice-Hall, Inc., 946 pages, Jul. 1995.
SIMFOR / CESOL, "'RV-Sold' Welding Simulator," Technical and Functional Features, 20 pages, estimated Jan. 2010.
Veiga, Issac Brana, Master's Thesis for "Simulation of a Work Cell in the IGRIP Program," Department of Applied Physics and Mechanical Engineering, Lulea University of Technology, 50 pages, Apr. 2006.
The Lincoln Electric Company, "VRTEX Virtual Reality Arc Welding Trainer," http://www.lincolnelectric.com/en-us/equipment/training-equipment/Pages/vrtex.aspx as accessed on Jul. 10, 2015, 3 pages.
Wade, Glen, "Human Uses of Ultrasound: Ancient and Modern," Ultrasonics, vol. 38, 5 pages, Mar. 2000.
Wang, Yizhong et al., "Study on Welder Training by Means of Haptic Guidance and Virtual Reality of Arc Welding," IEEE International Conference on Robotics and Biometrics, pp. 954-958, Dec. 17-20, 2006.
White, S. et al., Abstract for "Virtual Welder Trainer," Virtual Reality Conference, 2 pages, Mar. 14-18, 2009.
Yao, Ting et al., "Development of a Robot System for Pipe Welding," 2010 International Conference on Measuring Technology and Mechatronics Automation, pp. 1109-1112, Mar. 13-14, 2010.

\* cited by examiner

WELDING HELMET WITH INTEGRAL USER INTERFACE

CROSS-REFERENCE TO RELATED APPLICATIONS

This application is a continuation of and claims the benefit of U.S. application Ser. No. 12/577,824, filed Oct. 13, 2009, which is now issued as U.S. Pat. No. 8,569,655, granted Oct. 29, 2013.

TECHNICAL FIELD

This invention relates in general to equipment used in welding.

BACKGROUND

Welding is an important process in the manufacture and construction of various products and structures. Applications for welding are widespread and used throughout the world, for example, the construction and repair of ships, buildings, bridges, vehicles, and pipe lines, to name a few. Welding may performed in a variety of locations, such as in a factory with a fixed welding operation or on site with a portable welder.

In manual or semi-automated welding a user/operator (i.e. welder) directs welding equipment to make a weld. For example, in arc welding the welder may manually position a welding rod or welding wire and produce a heat generating arc at a weld location. In this type of welding the spacing of the electrode from the weld location is related to the arc produced and to the achievement of optimum melting/fusing of the base and welding rod or wire metals. The quality of such a weld is often directly dependent upon the skill of the welder.

Welders generally rely upon a variety of information when welding. This information includes, for example, current and voltage. Traditionally, welders would need to look at gauges on the control panel of the welding equipment to gain this information. This would require the welder to direct their field of vision away from the welding work area and as such was undesirable.

In the past, efforts have been made to provide welders with information during welding, such as in the method disclosed in U.S. Pat. No. 4,677,277, where current and voltage are monitored to produce an audio indication to the operator as to the condition of the arc in arc welding. However, monitors consisting only of audio arc parameter indicators are hard to hear and interpolate and are not capable of achieving the desired closeness of control and quality of weld often required.

More recently, as disclosed in U.S. Pat. No. 6,242,711, an apparatus for monitoring arc welding has been developed that provides a welder with real-time voltage and current conditions of the welding arc where information in the form of lights, illuminated bar graphs, light projections, illuminated see-through displays, or the like are placed within the visual range of the helmet wearing operator and located in proximity to the helmet viewing window in the helmet. However, in this apparatus a welder must still move their visual focus away from the welding work area in order to focus on the information located proximate to the welding window or the welder must accept the information peripherally while continuing to focus on the welding work area.

SUMMARY

This invention relates to a welding helmet that is capable of providing an image representative of information from an associated welding operation where the image appears in the same focal range as the welding work area.

Various aspects will become apparent to those skilled in the art from the following detailed description and the accompanying drawings.

DETAILED DESCRIPTION

Figure 1:
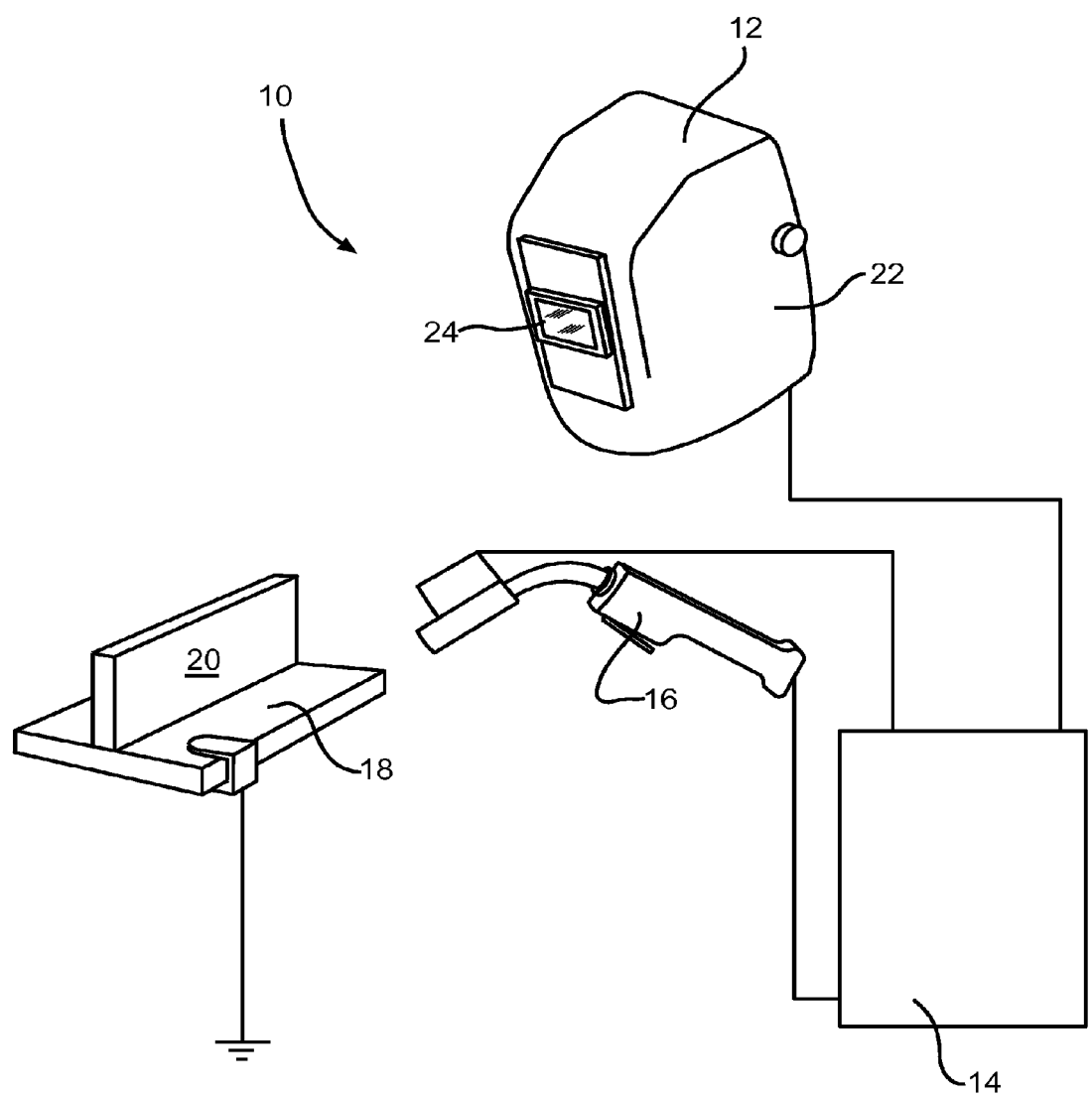
FIG. 1 is a schematic view of a welding system according to the present invention.

Referring now to the drawings, there is illustrated in FIG. 1 a welding system 10. The welding system 10 includes a welding helmet 12, a welding system 14, a welding gun 16 and a work piece 18. The work piece 18 generally defines a welding work are 20 where the welding gun 16 may be used to form a weld.

The welding system 14 includes welding equipment for generating a welding current and voltage, a welding control system for controlling the welding current and voltage, and a monitoring system for monitoring the welding current and voltage. The monitoring system may also monitor a variety of other operating parameter, such as but not limited to, wire feed speed, amount of wire used/amount of wire remaining, any type of welding feedback desired by the operator and any other desired operating parameter.

The welding helmet 12 includes a main body 22 with a visual display 24 connected to the main body 22. The display 24 may be a window including a welding lens, a video monitor, such as an LCD display or LED array, or any other device suitable to allow a welder to see the welding work area 20. It must be understood that in such an example where the display 24 is a video monitor video processing may be utilized to enhance the pictures of the welding operation. Further, recording devices may optionally be included to record and later playback welding operations for analysis and/or evaluation.

Figure 2:
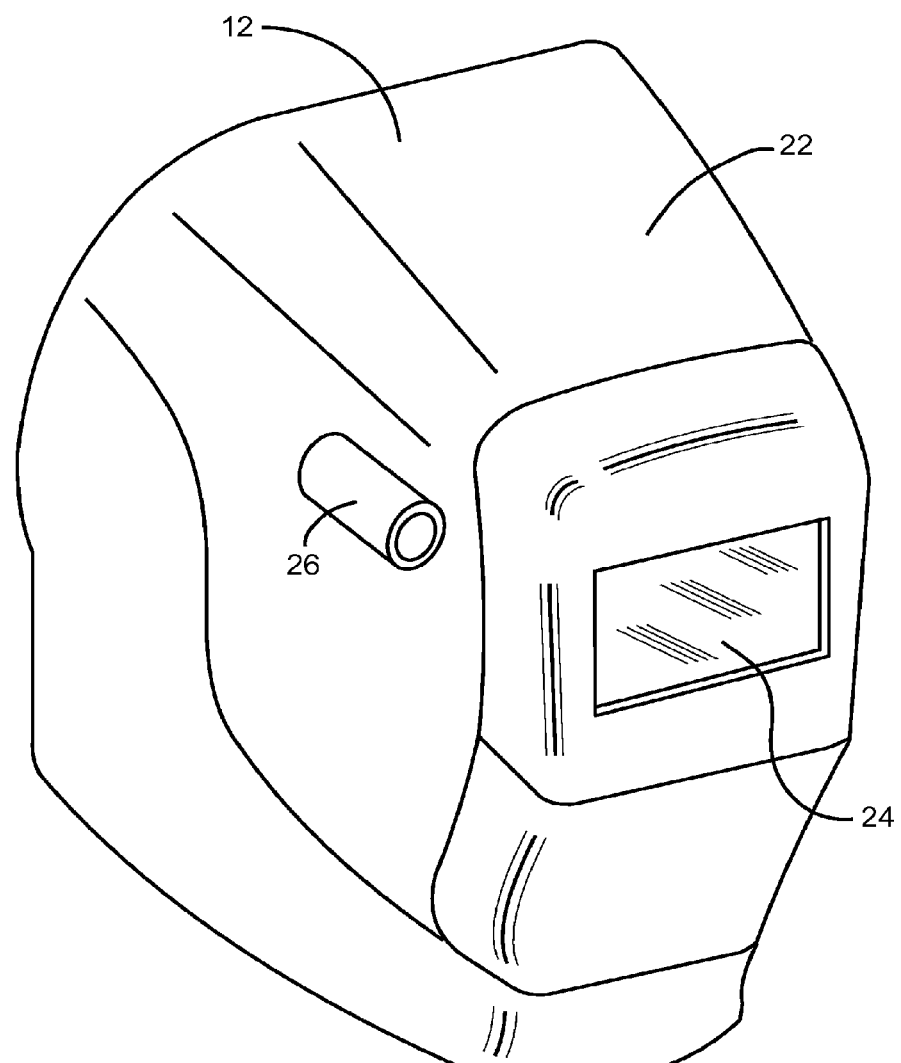
FIG. 2 is an enlarged view of a welding helmet similar to the helmet of FIG. 1 including a camera.

As best shown in FIG. 2, a welding helmet 12 may include a camera 26 mounted at or proximate to the point of view of the welder. In the example where the visual display 24 is a video monitor, the camera 26 may provide video pictures of the welding work area 20 to the display 24.

Figure 3:
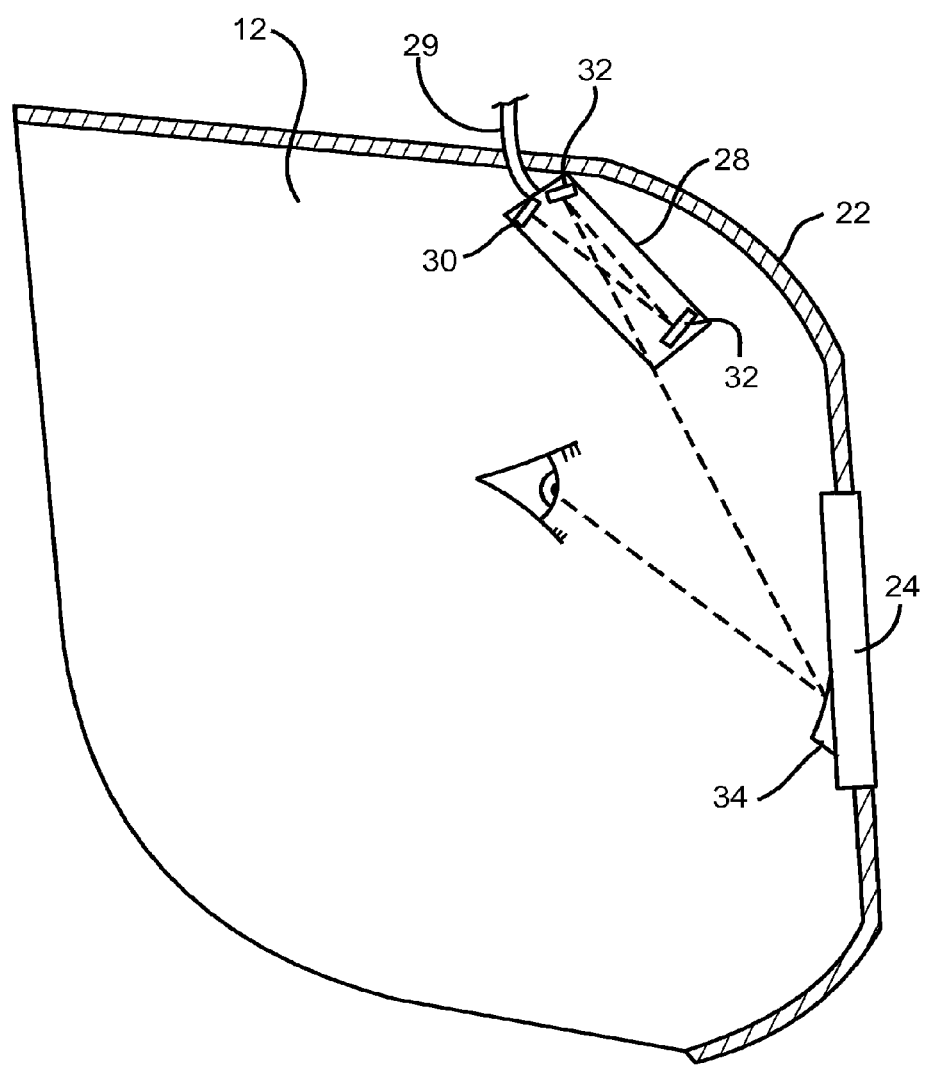
FIG. 3 is a cross-sectional diagram of a welding helmet similar to the helmet of FIG. 2 including a projector.
Figure 4:
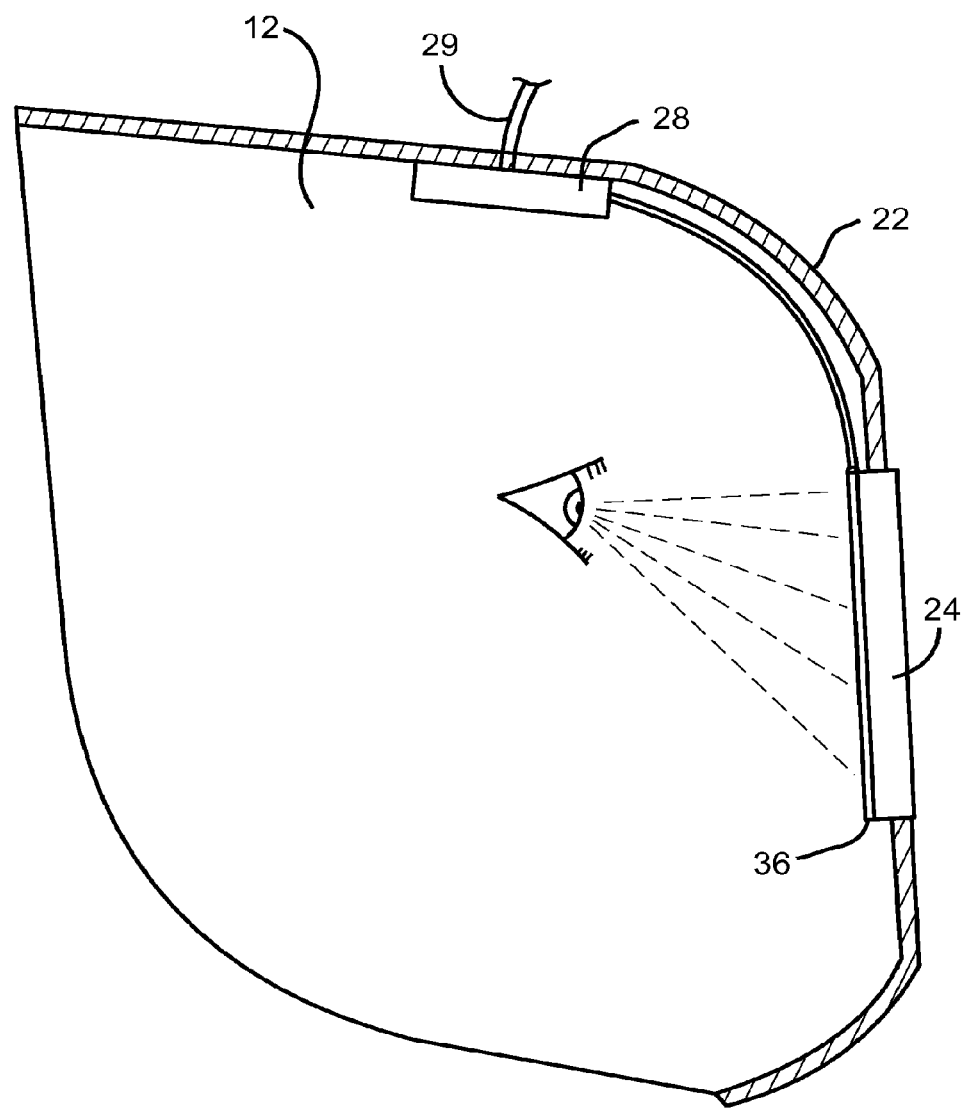
FIG. 4 is a cross-sectional diagram of a welding helmet similar to the helmet of FIG. 3 including an integrated video display.

As shown in FIGS. 3 and 4 an information generating mechanism 28 is in communication with the monitoring system of the welding system 14 and capable of generating an image representative of information from the monitoring system based upon the a monitored welding parameter, such as current and voltage upon the visual display 24 where the focus of the image is at a focus range with an associated welding work area, e.g. outside of the main body 22 of the welding helmet 12. For example, the image may be symbolic, alpha-numeric, or any other device suitable to indicate the information. Thus, a welder may view an image representative of information about a welding operation without removing focus from the work area. Thus, in at least one embodiment the welder may focus on the work area and the image of information at the same time.

It must be understood that among other types of information, along with a variety of other parameter, the information based upon welding current and voltage includes, but is not limited to, welding current feedback, welding voltage feedback, control settings of the welding equipment, statistical information of the welding process, benchmarks or limits including capacity representations, alerts including material shortage or low flow, a representation of an intended or desired weld, etc.

Further, in one embodiment, the camera 26 is used to calibrate the depth of the image relative to the welding work area 20. In another embodiment, positions sensors on the welding gun may be used to calibrate the depth of the image. In particular applications it is highly desirable to carefully align the image and the welding work are such that the information represented in the image is easy for the welder to access and such that the information in the image is readily accepted by the welder.

In the example where the visual display 24 is a video monitor, information generating mechanism 28 may include an image representative of information from the monitoring system based upon the monitored parameter, such as welding current and voltage, in video pictures of the welding work area 20 shown on the display 24.

As indicated at 29, the information generating mechanism 28 may be in wired or wireless communication with other devices as desired.

In FIG. 3, the information generating mechanism 28 is a projector 28. The projector may, for example, include an internal LCD display or LED array 30 along with a number of associated mirrors 32 to reflect the image generated to the visual display 24. The reflected image gives the image the appearance of depth relative to the visual display 24 and thus puts the image at a focus range with an associated welding work area and outside of the main body 22 of the welding helmet 12 and optionally at the same focal distance as the associated welding work area 20. Optionally, a reflective surface 34 may be placed upon a portion of the visual display 24 in order to achieve a desired amount of reflection or reflection angle. In one embodiment, teleprompter type technology may be utilized to place the image upon the display 24 or surface 34. Additionally, it must be understood that one embodiment includes the use of an LCD display or other similar display within the helmet to generate the image which is then sent along an optical path, such as by reflection or fiber optics or any other suitable device to place the image display 24 or surface 34.

In FIG. 4, the information generating mechanism 28 includes a screen, film, or sheet 36 integrated into the visual display 24. The sheet 36 may be a semi-transparent LCD film, electro-optic film, or any other suitable medium for the information generating mechanism 28 to produce an image generated in the visual display 24. In one application, the information generating mechanism 28 may projecting a stereogram on the welding lens such that a welder's eyes will separately view the images to create the perception of depth and thus focus the image at a focus range with the associated welding work area 20 and outside of the main body 22 of the welding helmet 12.

Figure 5:
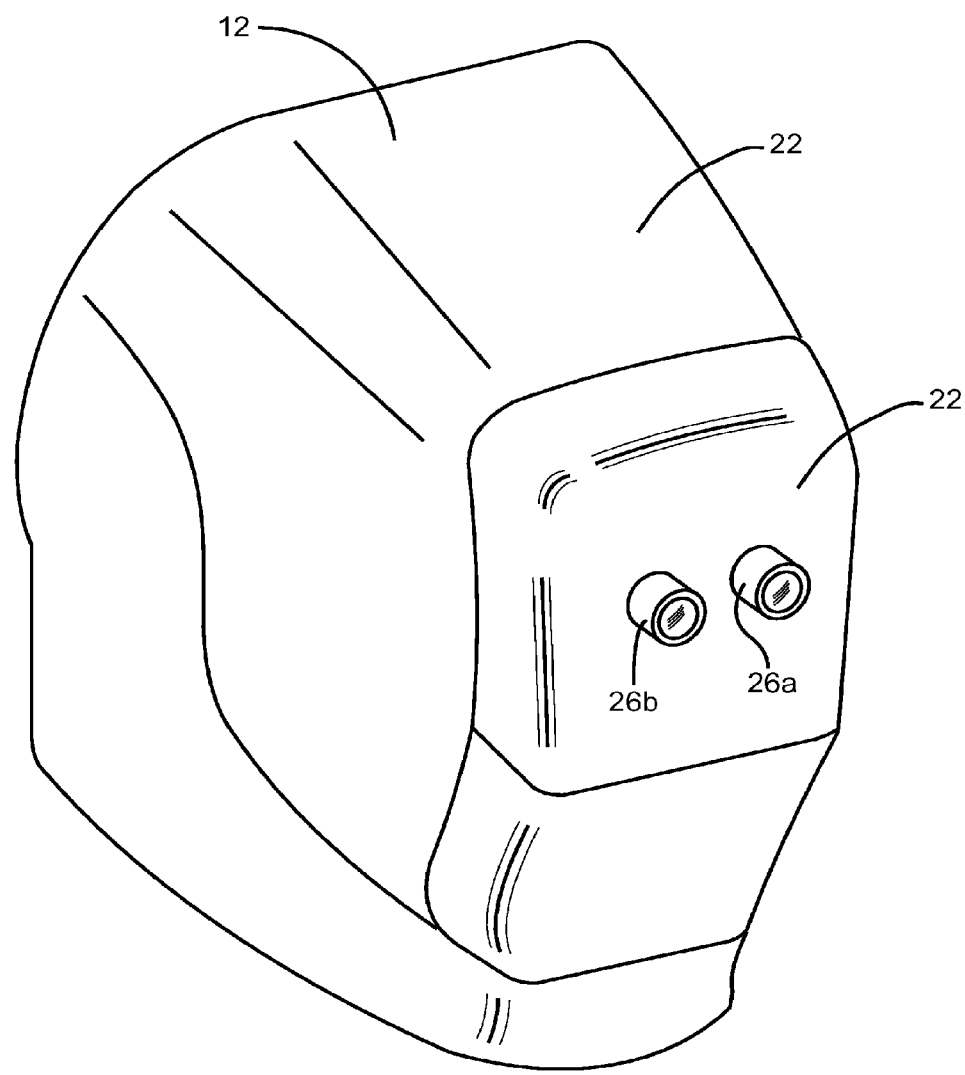
FIG. 5 is a perspective view of a welding helmet similar to the helmet of FIG. 2 including binocular cameras.
Figure 6:
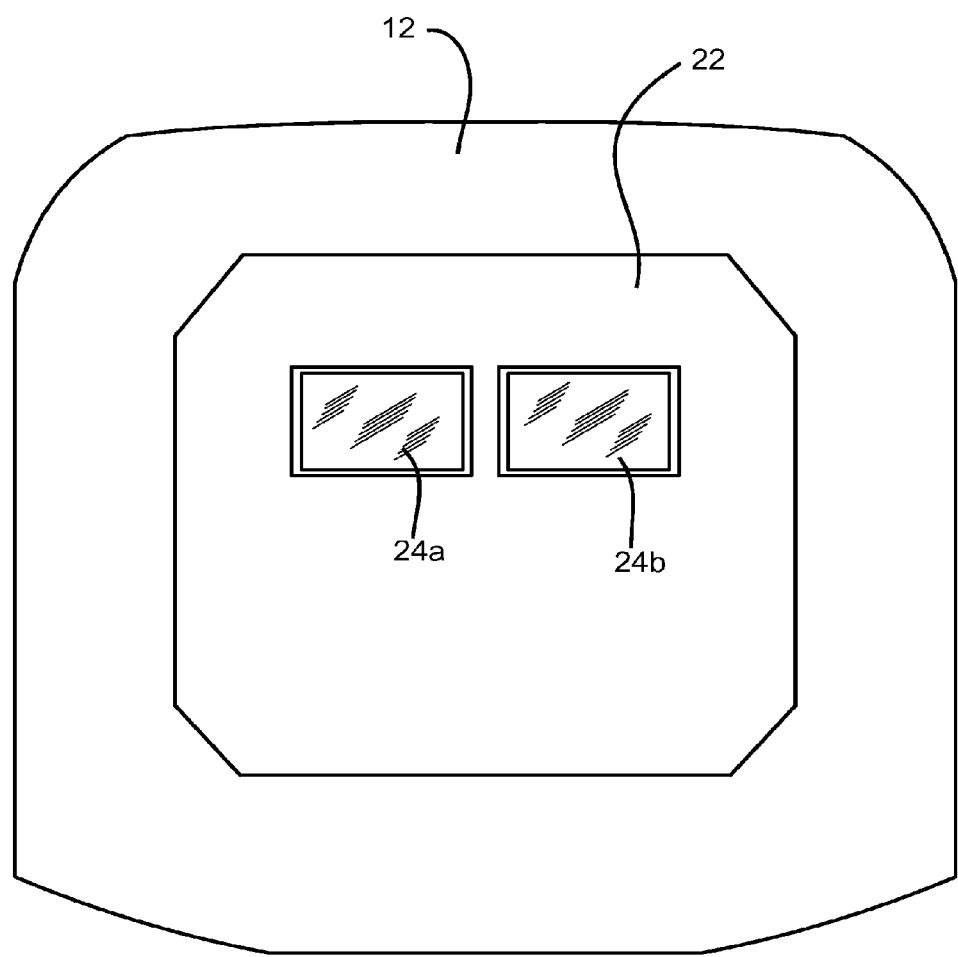
FIG. 6 is an interior view of a welding helmet similar to the helmet of FIG. 5 showing binocular viewing screens.

There is shown in FIG. 5 a welding helmet 12 including binocular cameras 26a and 26b. As shown in FIG. 6, these cameras 26a and 26b correspond to binocular viewing screens 24a and 24b. An information generating mechanism may produce an image to be generated in either of the viewing screens 24a or 24b or both. In one embodiment, the cameras 26a and 26b are placed in alignment with the screens 24a and 24b except on opposite sides of the main body 22, thus giving the welder the view directly in front of them. Additionally, in the embodiment with binocular cameras 26a and 26b and binocular viewing screens 24a and 24b the perception of depth of filed is produced.

In any case, the image may be an overlay of text or graphics or video feedback. Additionally, it is contemplated that in at least one embodiment the system described above may be used in a remote welding situation, including but not limited to robotic welding or underwater welding.

While principles and modes of operation have been explained and illustrated with regard to particular embodiments, it must be understood, however, that this may be practiced otherwise than as specifically explained and illustrated without departing from its spirit or scope.

What is claimed is:

1. A welding helmet comprising:
  a main body portion;
  a visual display portion connected to the main body portion, the visual display portion defining a viewing area; and
  an information generating mechanism which generates an image on the visual display portion, said image being viewable during a welding operation, wherein a focus of the image is at a focus range associated to a work area of the welding operation.

2. The welding helmet of claim 1, wherein information displayed in the image includes at least one of a welding current, welding voltage, welding control parameter, welding equipment, statistical information, control settings, capacity representations, alerts, and a representation of a weld.

3. The welding helmet of claim 1 further comprising a camera adapted to view and record a welding operation in the work area, the camera being used to record a welding operation in the work area.

4. The welding helmet of claim 1, wherein the image includes an image of the welding operation.

5. The welding helmet of claim 1, wherein the visual display portion allows the welding operation to be viewed at least through at least a portion of the visual display portion.

6. The welding helmet of claim 1, wherein the information generating mechanism is a projector.

7. The welding helmet of claim 1, wherein the visual display portion includes at least one reflective surface.

8. The welding helmet of claim 1, wherein the visual display includes at least one mirror.

9. The welding helmet of claim 1, wherein the image generating mechanism includes at least one of a screen, a film, and a sheet integrated into the visual display portion.

10. The welding helmet of claim 9, wherein the film includes at least one of a semi-transparent LCD film and an electro-optic film.

11. The welding helmet of claim 1, wherein the information generating mechanism includes a stereo projection, including separate images adapted to create a perception of depth.

12. A welding helmet comprising:
  a main body portion;
  a visual display portion connected to the main body portion, the visual display portion defining a viewing area;
  an information generating mechanism which generates an image on the visual display portion, said image being viewable during a welding operation, wherein a focus of the image is at a focus range associated to a work area of the welding operation; and a camera adapted to view the work area, wherein the camera is connected to the visual display portion to calibrate a depth of the image relative to the work area.

13. A welding helmet comprising:

a main body portion;

a visual display portion connected to the main body portion, the visual display portion defining a viewing area;

an information generating mechanism which generates an image on the visual display portion, said image being viewable during a welding operation, wherein a focus of the image is at a focus range associated to a work area of the welding operation; and a sensor located outside of said main body portion and in communication with said visual display portion to calibrate a depth of the image.

* * * * *